US011684685B1

(12) United States Patent
Gonzalez et al.

(10) Patent No.: US 11,684,685 B1
(45) Date of Patent: Jun. 27, 2023

(54) ULTRAVIOLET LIGHT SANITIZER

(71) Applicant: UVC SUNSHADE LLC, Kansas City, MO (US)

(72) Inventors: Cesar N. Gonzalez, Fairway, KS (US); Aaron J. Schlagel, Kansas City, MO (US); John F. Cooney, Jr., Palm Beach, FL (US)

(73) Assignee: UVC SUNSHADE LLC, Kansas City, MO (US)

( * ) Notice: Subject to any disclaimer, the term of this patent is extended or adjusted under 35 U.S.C. 154(b) by 227 days.

(21) Appl. No.: 17/190,922

(22) Filed: Mar. 3, 2021

Related U.S. Application Data

(60) Provisional application No. 63/018,565, filed on May 1, 2020.

(51) Int. Cl.
*A61L 2/10* (2006.01)

(52) U.S. Cl.
CPC .............. *A61L 2/10* (2013.01); *A61L 2202/11* (2013.01); *A61L 2202/14* (2013.01); *A61L 2202/16* (2013.01); *A61L 2202/25* (2013.01)

(58) Field of Classification Search
CPC .......... A61L 2/10; A61L 2/26; A61L 2202/16; A61L 2202/25
See application file for complete search history.

(56) References Cited

U.S. PATENT DOCUMENTS

| 9,371,033 B2 | 6/2016 | Lock et al. | |
| 2011/0243789 A1* | 10/2011 | Roberts | A61L 2/10 422/116 |
| 2012/0311881 A1* | 12/2012 | Lin | A61L 2/10 34/90 |

(Continued)

FOREIGN PATENT DOCUMENTS

| BR | 102017017951-6 | 4/2018 |
| CN | 102018988 | 12/2010 |
| CN | 105920632 | 2/2016 |

(Continued)

OTHER PUBLICATIONS

Article, "Seoul Viosys' Violeds Technology Adopted for Interior Automotive Disinfection", LEDinside of TrendForce Corp., Apr. 9, 2020, downloaded from the internet at hps://www.ledinside.com/news/2020/4/uvled_automotive on Apr. 23, 2020 (3 pgs).

(Continued)

*Primary Examiner* — Eliza W Osenbaugh-Stewart
(74) *Attorney, Agent, or Firm* — Stinson LLP

(57) ABSTRACT

A sanitizer including a base that is at least one of flexible or foldable, and an ultraviolet (UV) light source configured to emit UV light and coupled to the base. The base of the sanitizer may be configured to be removably placed over a window of a vehicle such that UV light emitted from the sanitizer sanitizes surfaces within the interior of the vehicle and items placed within the vehicle. A sanitizer having a base that is movable from a deployed position in which it covers a storage compartment of a vehicle to an access position. A UV light source coupled to the base is configured to emit UV light. The UV light source is configured to emit UV light into the storage compartment when the base is in the deployed position.

7 Claims, 10 Drawing Sheets

(56) References Cited

U.S. PATENT DOCUMENTS

2018/0185529 A1* 7/2018 Shur .................. A61L 2/24
2019/0137056 A1* 5/2019 Sreshta ................ H02J 7/35

FOREIGN PATENT DOCUMENTS

| | | |
|---|---|---|
| CN | 108621925 | 4/2018 |
| DE | 10 2004 027 317 A1 | 12/2004 |
| DE | 10 2012 006 972 A1 | 10/2013 |
| DE | 20 2018 001 847 U1 | 8/2019 |
| JP | 2017-158829 | 9/2017 |
| KR | 20-2011-006422 | 6/2011 |
| KR | 10-1330667 | 11/2013 |
| KR | 10-1650093 | 7/2016 |
| KR | 10-1816255 | 1/2018 |
| KR | 10-2019-0093081 | 8/2019 |
| KR | 10-2019-0132737 | 11/2019 |

OTHER PUBLICATIONS

Blog Article, "Disinfecting EMS Vehicles with Ultraviolet Light", Frazer, Ltd., Mar. 11, 2020, downloaded from the internet at https://www.frazerbilt.com/blog-ambulance-disinfection-system/ on Apr. 23, 2020 (5 pgs).

* cited by examiner

ULTRAVIOLET LIGHT SANITIZER

CROSS-REFERENCE TO RELATED APPLICATIONS

This application is based on and claims priority to U.S. Provisional Application Ser. No. 63/018,565, filed on May 1, 2020, which is incorporated herein by reference in its entirety.

BACKGROUND OF THE INVENTION

1. Field of the Invention

The invention relates to sanitizers and, in particular, to ultraviolet light sanitizers.

2. Description of Related Art

It is generally known that ultraviolet (UV) light, and in particular UV light having a wavelength associated with UVC light, is capable of killing microorganisms such as pathogens, viruses, germs, bacteria, and molds. UV light sources, such as light bulbs and light emitting diodes, have been developed and incorporated into products designed to sanitize surfaces and objects by killing harmful microorganisms.

One such product is a sanitizer with an enclosable compartment that is designed to hold a mobile phone and sanitize surfaces of the phone. Another such product is a sanitizer shaped as a small bag with an enclosable compartment that may hold smaller items such as keys, jewelry, eyeglasses, and remote controls. While these products are believed to be generally suitable for their intended purposes, there are many types of objects and surfaces, on which harmful microorganisms may be present, that are too large to be placed within the enclosable compartments of these products. For example, these products cannot sanitize large bags of groceries or store-bought items. Further, these products cannot sanitize large surface areas, such as the surfaces found within a typical automobile, e.g., car seats, steering wheel, center console, glove box, window controls, transmission control levers, etc.

There are also products that have been developed for sanitizing certain interior surfaces of a car. These conventional car sanitizers include a UV light that is mounted to a ceiling of the car. While these conventional car sanitizers may be generally suitable for sanitizing certain interior surfaces of a car that are in the path of UV light emitted from the ceiling, the conventional car sanitizers cannot be used in a versatile manner to sanitize surfaces and objects that are not positioned in the path of UV light emitted from the ceiling or surfaces and objects that are positioned outside of the vehicle. Further, it may be expensive and timely to mount the conventional car sanitizers to the ceiling of a car and connect them to the electrical wiring of the car.

BRIEF SUMMARY OF THE INVENTION

One embodiment of the invention described herein is directed toward a sanitizer including a base that is at least one of flexible or foldable, and an ultraviolet (UV) light source configured to emit UV light and coupled to the base. The UV light source may be configured to emit UV germicidal irradiation and include one or more of a low pressure mercury discharge lamp, one or more fiber optic couplings, or one or more light emitting diodes.

In one exemplary embodiment, the base of the sanitizer is configured to be removably placed over a window of a vehicle (e.g., the windshield of a vehicle in a similar manner as a conventional sunshade). In such a configuration, UV light emitted from the sanitizer may be used to sanitize surfaces within the interior of the vehicle and items placed within the vehicle. The base may be foldable. The base may include a top edge, a bottom edge, a first side edge, and a second side edge. The base may include a plurality of rigid or semi-rigid sections and a plurality of flexible sections. The base may be foldable from a first position in which it is generally planar into a second position in which it is generally cylindrical and the first side edge is positioned adjacent the second side edge. In the generally cylindrical orientation, items such as grocery bags may be placed within an interior cavity defined by the base for sanitizing the items. The plurality of flexible sections may include a bottom flexible section that is spaced apart from the bottom edge and that extends from adjacent the first side edge to adjacent the second side edge. The plurality of rigid or semi-rigid sections may include at least one bottom section positioned between the bottom edge and the bottom flexible section. The bottom flexible section may be configured so that the at least one bottom section may be folded to extend laterally outward from an adjacent portion of the base to provide stability for the sanitizer to be used on a freestanding basis. The sanitizer may further include a first attachment structure coupled to the base adjacent the first side edge and a second attachment structure coupled to the base adjacent the second side edge. The first attachment structure may be configured to releasably attach to the second attachment structure.

In one exemplary embodiment, the base may include a flexible sheet of material. For example, the base may resemble a blanket or sheet that may be draped over items for sanitizing the items beneath the base.

A battery may be coupled to the base and electrically coupled to the UV light source. At least one solar panel may be coupled to the base and electrically coupled to the battery. A controller may be electrically coupled to the UV light source. A sensor may be coupled to the base and electrically coupled to the controller. The sensor being configured to detect when a person is near the base and transmit a safety signal to the controller. The controller may be configured to turn off the UV light source when it receives the safety signal.

Another exemplary embodiment of the invention described herein is directed toward a sanitizer having a base that is movable from a deployed position in which it covers a storage compartment of a vehicle to an access position. An ultraviolet (UV) light source coupled to the base is configured to emit UV light. The UV light source is configured to emit UV light into the storage compartment when the base is in the deployed position. The storage compartment may be one of a truck bed compartment, a rear cargo compartment of the vehicle, a trunk of the vehicle, a glove box of the vehicle, or a center console compartment of the vehicle.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
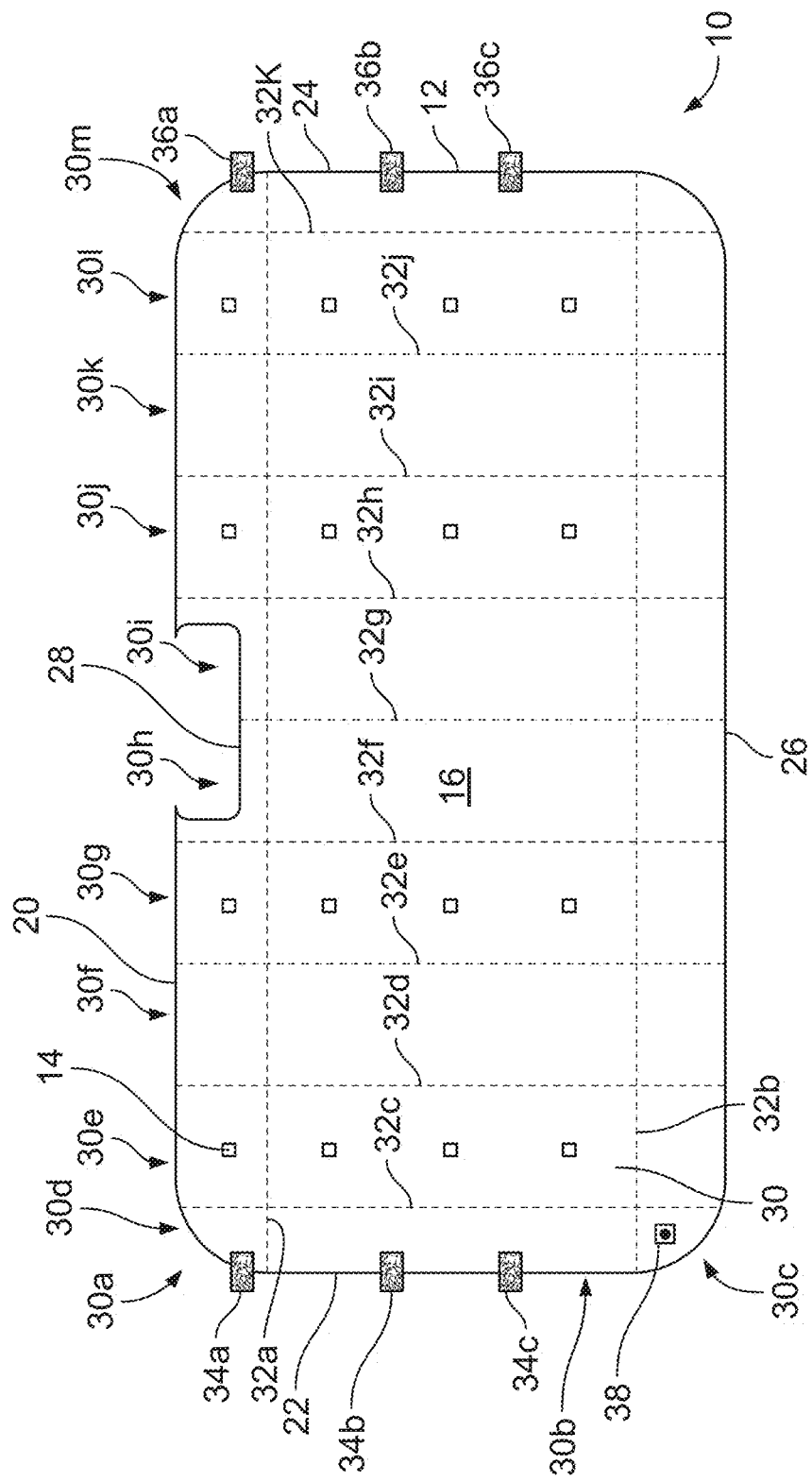
FIG. 1 is a front elevational view of an exemplary embodiment of UV light sanitizer in accordance with the invention described herein.

FIGS. 1-4 show an exemplary embodiment of ultraviolet (UV) light sanitizer 10 in accordance with the invention described herein. Sanitizer 10 includes a base 12 that is formed in the shape of a sunshade for a vehicle, such as an automobile or truck. UV light sources, one of which is identified as 14 in FIG. 1, are attached to the base 12. The UV light sources 14 are configured to emit UV light to sanitize surfaces or items positioned in the path of the emitted UV light as described in more detail below.

The base 12 is configured to be removably placed over the interior of a vehicle's windshield to substantially cover the windshield. The base 12 includes a front surface 16, shown in FIG. 1, and a rear surface 18, shown in FIG. 2. The front surface 16 is designed to face the interior of a vehicle when the base 12 is positioned to cover the vehicle's windshield, and the rear surface 18 is designed to face the vehicle's windshield. The UV light sources 14 are attached to the base 12, as shown in FIG. 1, so that they are capable of emitting UV light outward and away from the front surface 16. The base 12 and UV light sources 14 are configured so that no appreciable amount of UV light is emitted from the UV light sources 14 through the base 12 and outward from the rear surface 18.

The base 12 has a top edge 20, a first side edge 22, a second side edge 24, and a bottom edge 26. The base 12 is generally rectangular in shape with the top edge 20 and bottom edge 26 being longer than the side edges 22 and 24. The base 12 has rounded corners between the top edge 20, first side edge 22, second side edge 24, and bottom edge 26.

A cutout 28 is positioned at approximately the midpoint of the top edge 20 so that the base 12 may fit around a rear view mirror when the base 12 is positioned to cover a vehicle's windshield.

The base 12 includes a plurality of rigid or semi-rigid sections, one of which is identified as 30 in FIG. 1, and a plurality of flexible sections 32a-k. The plurality of flexible sections 32a-k are shown as dashed lines in FIG. 1, and the plurality of rigid or semi-rigid sections 30 are shown as white space positioned in between the dashed lines. As shown in FIG. 1, the plurality of rigid or semi-rigid sections 30 includes a top row 30a, a middle row 30b, and a bottom row 30c. Further, each of the top row 30a, middle row 30b, and bottom row 30c are divided into ten columns 30d-30m forming a total of thirty rigid or semi-rigid sections 30. The top flexible section 32a and the bottom flexible section 32b extend from first side edge 22 to second side edge 24 and are generally parallel to top edge 20 and bottom edge 26. The top flexible section 32a is spaced apart from the top edge 20 a distance that is about one-fifth of the height of base 12 from top edge 20 to bottom edge 26, and the bottom flexible section 32b is spaced apart from the bottom edge 26 a distance that is about one-fifth of the height of base 12. Thus, the top and bottom rows 30a and 30c of rigid or semi-rigid sections each have a height that is approximately one-fifth of the height of base 12 and the middle row 30b has a height that is approximately three-fifths of the height of base 12. The top flexible section 32a and bottom flexible section 32b are generally horizontal when the base 12 is placed on a vehicle windshield. The flexible sections 32c-k each extend from top edge 20 to bottom edge 26. The flexible sections 32c-k are generally vertical when the base 12 is placed on a vehicle windshield. The flexible sections 32c-k are spaced approximately equidistant from each other across the width of the base 12 from first side edge 22 to second side edge 24.

The top row 30a of rigid or semi-rigid sections 30 is positioned between the top edge 20 and top flexible section 32a, the middle row 30b is positioned between the flexible sections 32a-b, and the bottom row 30c is positioned between the bottom flexible section 32b and the bottom edge 26. The column 30d of rigid or semi-rigid sections 30 is positioned between the first side edge 22 and the flexible section 32c, the columns 30e-30l are each positioned between adjacent flexible sections 32c-32k, and the column 30m is positioned between the flexible section 32k and the second side edge 24.

Figure 2:
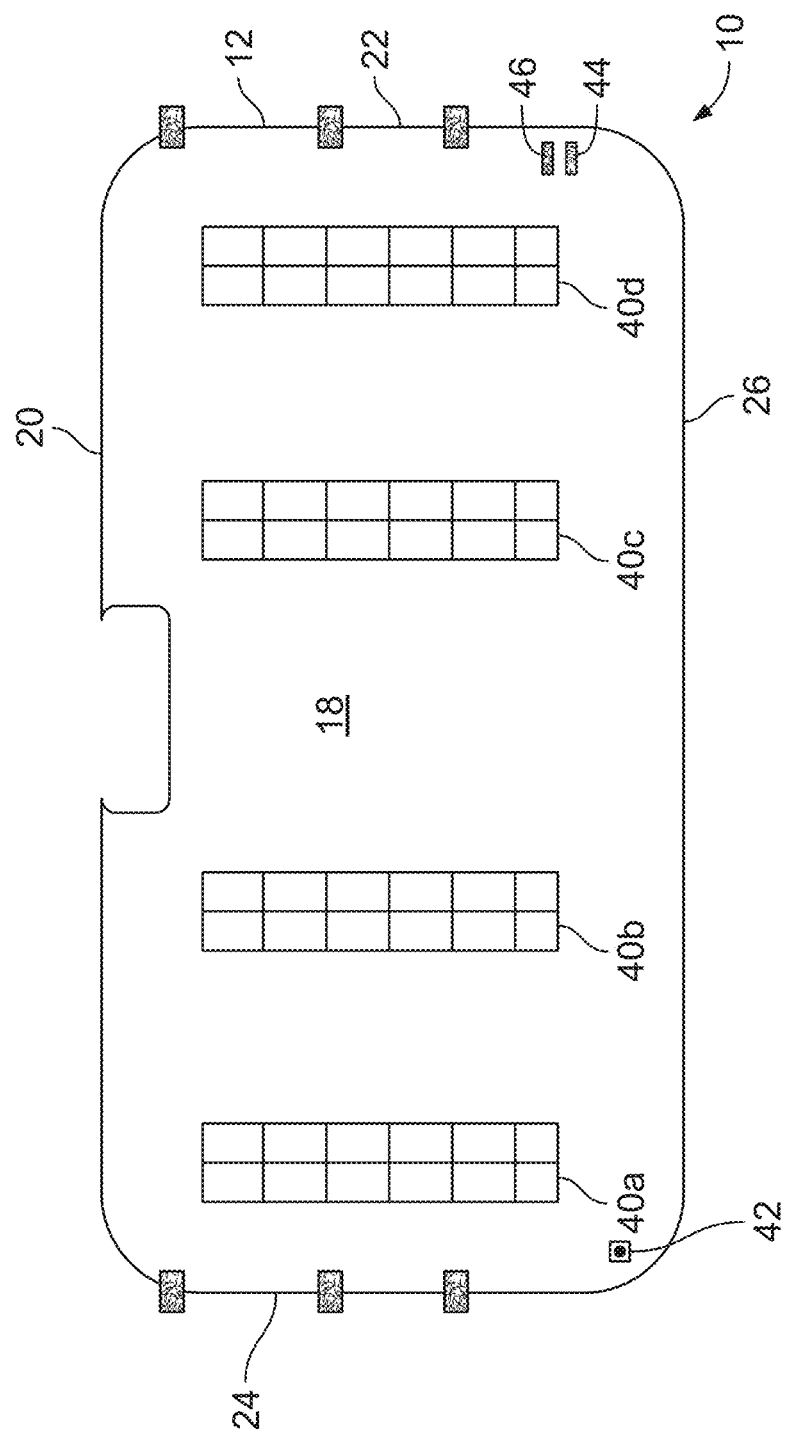
FIG. 2 is a rear elevational view of the UV light sanitizer of FIG. 1.
Figure 3:
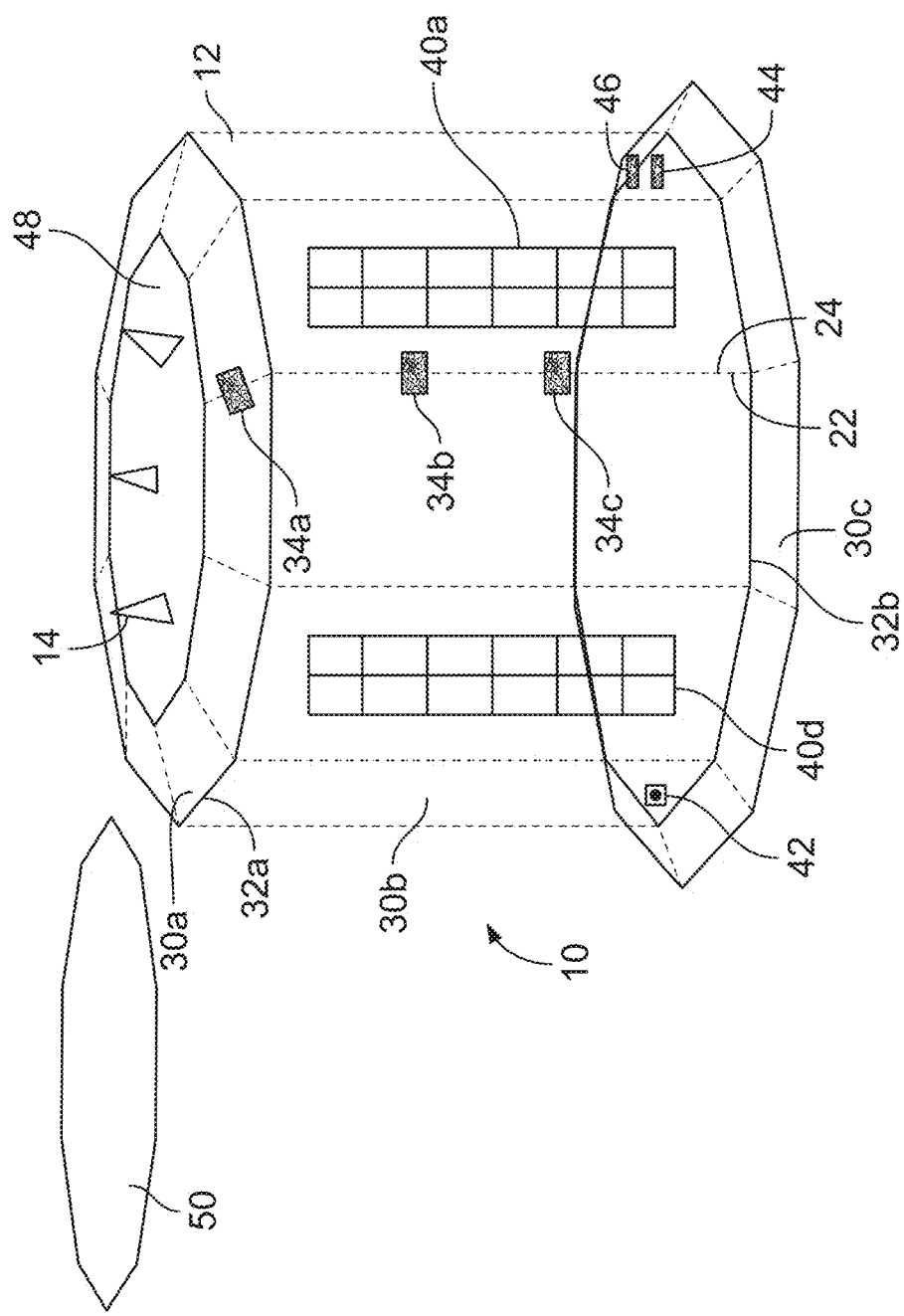
FIG. 3 is a perspective view of the UV light sanitizer of FIG. 1 showing the sanitizer in an alternate position from the position shown in FIGS. 1 and 2.
Figure 4:
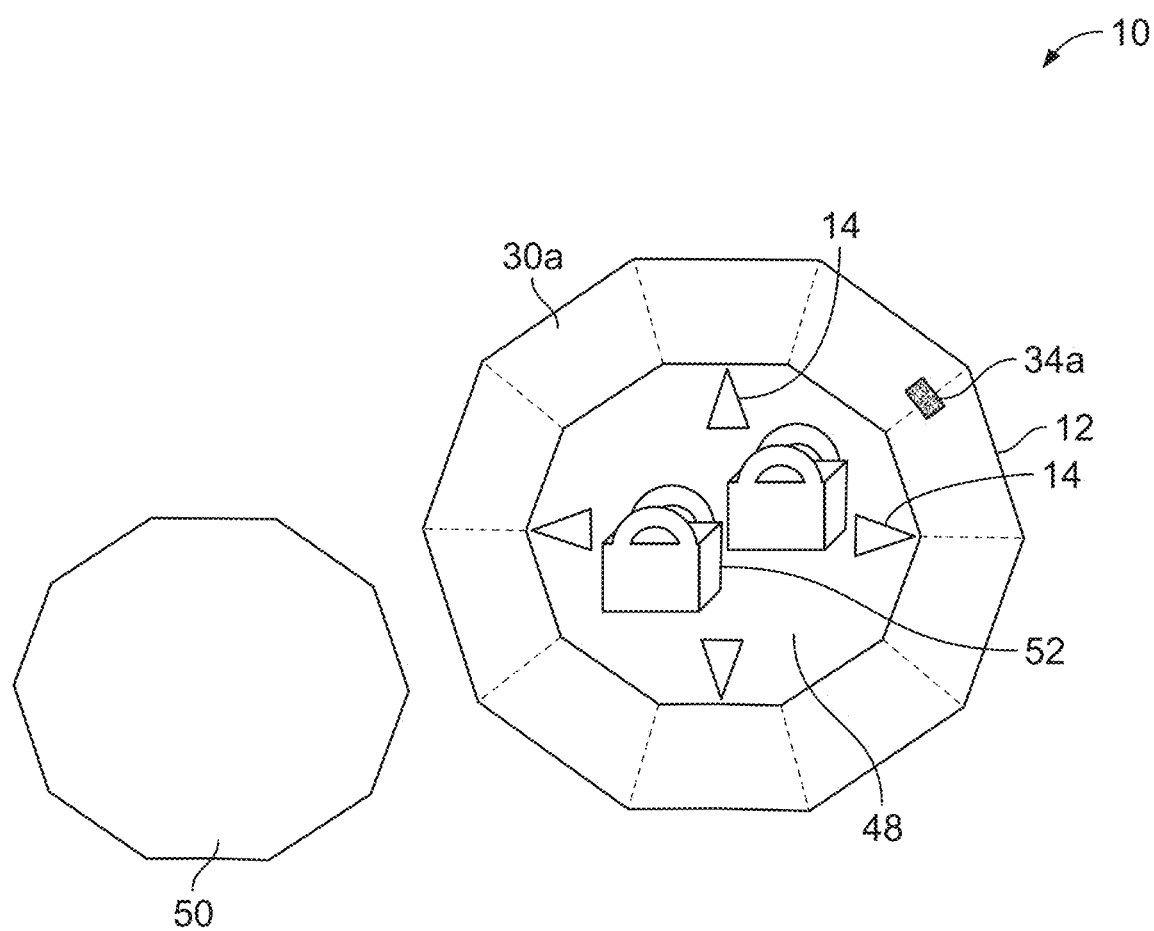
FIG. 4 is a top plan view of the UV light sanitizer of FIG. 1 shown in the alternate position of FIG. 3.

In one exemplary embodiment, the base 12 may be formed from two or more sheets of flexible material that are joined together (e.g., by sewing) along edges 20, 22, 24, and 26 and at flexible sections 32a-k to form pockets between the edges 20, 22, 24, and 26 and flexible sections 32a-k. Pieces of rigid or semi-rigid material may be placed within the pockets to form the rigid or semi-rigid sections 30. For example, the sheets of flexible material may be sheets of fabric that are woven or non-woven and formed from synthetic polymers or natural materials. The rigid or semi-rigid material may be any suitable material, such as a polymeric foam. When used herein, "rigid or semi-rigid" means that when a bending force is applied to the base 12, the base 12 bends or folds at the flexible sections 32a-k while the rigid or semi-rigid sections 30 largely retain their shape. The flexible sections 32a-k allow the base 12 to fold into a variety of different shapes. For example, the base 12 may be used in a generally planar shape, as shown in FIGS. 1 and 2, or the base 12 may be used in a generally cylindrical shape, as shown in FIGS. 3 and 4 and described in more detail below. The base 12 may also be folded into a more compact shape for storage by alternately folding it in different directions along the flexible sections 32c-k, i.e., an accordion fold.

While base 12 is shown and described above with three rows 30a-c and ten columns 30d-m of rigid or semi-rigid sections 30, any numbers of rows 30a-c and columns 30d-m are within the scope of the invention. For example, there may be only one row of rigid or semi-rigid sections if flexible sections 32a-b are omitted. There may also only be one column of rigid or semi-rigid sections 30 if flexible sections 32c-k are omitted.

Further, as shown in FIG. 1, three straps 34a-c are joined to the base 12 adjacent the first side edge 22, and three straps 36a-c are joined to the base adjacent the second side edge 24. The straps 34a-c may include hook material, while the straps 36a-c may include loop material configured to engage the hook material of straps 34a-c, respectively. The straps 34a-c may be joined to the straps 36a-c, respectively, to join the first side edge 22 to the second side edge 24, as shown in FIGS. 3 and 4 and described in more detail below. While three straps are shown joined to each side edge 22 and 24, the sanitizer 10 may have more or less than three straps on each side. Further, other types of attachment structures may be used to releasably attach first side edge 22 to second side edge 24 other than straps with hook and loop material. For example, snaps may be joined to base 12 adjacent first side edge 22 and second side edge 24. In some embodiments, the sanitizer 10 may not include any attachment structures configured to attach first side edge 22 to second side edge 24.

As shown in FIG. 1, sanitizer 10 includes sixteen UV light sources 14, which includes four each in the columns 30e, 30g, 30j, and 30l. Further, four of the UV light sources 14 are positioned in the top row 30a, and twelve are positioned in the middle row 30b. The number and positioning of UV light sources 14 shown in FIG. 1 is exemplary, and the sanitizer 10 may include any number of UV light sources 14 in any position or pattern on the base 12.

A button 38 is positioned in the lower left hand corner of the front surface 16 of base 12. The button 38 may be used to turn the UV light sources 14 on and off, as described in more detail below. The button 38 may alternatively be a switch or any type of user input device that allows for the UV light sources 14 to be turned on and off.

Referring now to FIG. 2, the rear surface 18 of base 12 includes four solar panels 40a-d. While the flexible sections 32a-k are not shown in FIG. 2 for clarity, the solar panels 40a-d are positioned so that they are each joined to one of the rigid or semi-rigid sections 30 to not impede bending of the base 12 at the flexible sections 32a-k. When sanitizer 10 is placed on a vehicle windshield, the solar panels 40 face the windshield and are exposed to sunlight entering the windshield. The solar panels 40 are configured to convert solar energy into electrical energy, which may be stored in batteries that are formed as part of the solar panels 40 or that are separate from the solar panels 40 and electrically connected to the solar panels 40. The rear surface 18 of base 12 may be formed from a reflective material to reflect sunlight away from the vehicle, similar to a conventional vehicle sunshade. A button 42 is positioned in the lower left hand corner of the rear surface 18 of base 12. Like the button 38, the button 42 may be used to turn the UV light sources 14 on and off, as described in more detail below. The button 42 may alternatively be a switch or any type of user input device that allows for the UV light sources 14 to be turned on and off. FIG. 2 also shows a pair of electrical connectors 44 and 46 positioned in a lower right hand corner of rear surface 18. The electrical connectors 44 and 46 may be electrically connected to one or more batteries of the sanitizer 10. The electrical connector 44 may be configured for connection to a source of power to charge the batteries and/or power the UV light sources 14, while the electrical connector 46 may be configured for connection to a device that draws power from the batteries. The electrical connectors 44 and 46 may be any suitable type of electrical connector, e.g., any type of USB connector, that may deliver power to and from the batteries and/or UV light sources 14.

The base 12 is foldable from the generally planar position shown in FIGS. 1-2 to the generally cylindrical position shown in FIGS. 3-4 due to the flexible sections 32a-k. In the generally cylindrical position, the base 12 defines an interior cavity 48 within which items may be placed for sanitization. In the generally cylindrical position, the first side edge 22 is positioned adjacent the second side edge 24 and the side edges 22 and 24 are joined with the straps 34a-c, 36a-c. Only straps 34a-c are shown in FIG. 3 since they may overlay the straps 36a-c when joined together. Further, it should be noted that button 42 and electrical connectors 44, 46 are shown in alternate positions in FIG. 3 from the positions shown in FIG. 2, which is exemplary of the fact that the button 42 and electrical connectors 44, 46 may be placed in any suitable location on the base 12.

As shown in FIG. 3, the bottom flexible section 32b is folded so that the bottom section or row 30c of rigid or semi-rigid sections 30 extends laterally outward from the middle row 30b while the middle row 30b is generally vertically oriented. In this position, the front surface 16 of the bottom row 30c may be generally horizontal and placed on a surface to support the remainder of base 12 above it. As shown in FIG. 3, the bottom row 30c is positioned outside of the interior cavity 48; however, the bottom row 30c may also be folded inward so that it is positioned inside at the bottom of the interior cavity 48. The top row 30a may be folded inward along the top flexible section 32a so that the top row 30a extends laterally inward from the middle row 30b. When UV light sources 14 are placed on the front surface 16 of the top row 30a, as shown in FIG. 1, the UV light sources 14 on the top row 30a face downward when the top row 30a is bent into the position shown in FIG. 3. The UV light sources 14 on the top row 30a may thus shine directly down on top of items positioned within the interior cavity 48 to increase exposure to the UV light emitted from the UV light sources 14. Further, when top row 30a is bent into the position shown in FIG. 3, it may be used to support a lid 50. The lid 50 may be placed on the top row 30a to substantially enclose the interior cavity 48 so that UV light emitted from UV light sources 14 remains within the interior cavity 48. Use of the lid 50 may increase the safety of sanitizer 10 by preventing exposure to UV light, and use of the lid 50 may also increase the efficacy of sanitizer 10 by directing more of the UV light emitted onto items placed within the interior cavity 48.

FIG. 4 shows grocery bags 52 positioned within the interior cavity 48 formed by base 12. When lid 50 is supported by the top row 30a, the interior cavity 48 is substantially enclosed so that UV light emitted from UV light sources 14 is directed toward the grocery bags 52 for sanitizing the bags 52 and contents within the bags 52. It should be understood that other items besides grocery bags 52 may be placed within the interior cavity 48 for sanitization. Further, the size of the base 12 may be configured so that items of a certain size may be placed within interior cavity 48. Further, more than one base 12 may be joined together using straps 34a-c and 36a-c to form an interior cavity 48 of a larger size than if only one base 12 was used.

For example, the straps 34*a-c* on a first base 12 may be joined to the straps 36*a-c* on a second base 12, and the straps 36*a-c* of the first base 12 may be joined to the straps 34*a-c* of the second base 12. The base 12 may be used in the position shown in FIGS. 3 and 4 within a vehicle interior (e.g., on a seat or floor of the vehicle, or in a rear cargo compartment of the vehicle behind a rear seat), in a vehicle trunk, or in the bed of a truck. When used in this manner, the electrical connector 44 may be joined to a source of power from the vehicle for continuously powering the UV light sources 14. For example, the electrical connector 44 may be joined with an electrical cable to a 12V socket (e.g., cigarette lighter socket) or a USB connector of the vehicle, which in turn is connected to the vehicle's electrical system and battery. An internal battery of the sanitizer 10 and/or the solar panels 40*a-d* may also be used to power the UV light sources 14 for using the sanitizer 10 inside or outside of a vehicle.

The UV light sources 14 are configured to emit UV germicidal irradiation, and they may include one or more of a low pressure mercury discharge lamp, one or more fiber optic couplings, or one or more light emitting diodes. UV germicidal irradiation uses UV light at one or more wavelengths to kill microorganisms. For example, the UV light sources 14 may emit short-wavelength UV radiation that destroys nucleic acids in various microorganisms, leaving them unable to perform cellular functions. In general, the UV light sources 14 are configured to emit UV light that kills microorganisms, including pathogens, viruses, germs, bacteria, and molds, for example. The UV light sources 14 may emit UV light with wavelengths associated with one or more of ultraviolet A (UVA), ultraviolet B (UVB), and/or ultraviolet C (UVC).

Figure 5:
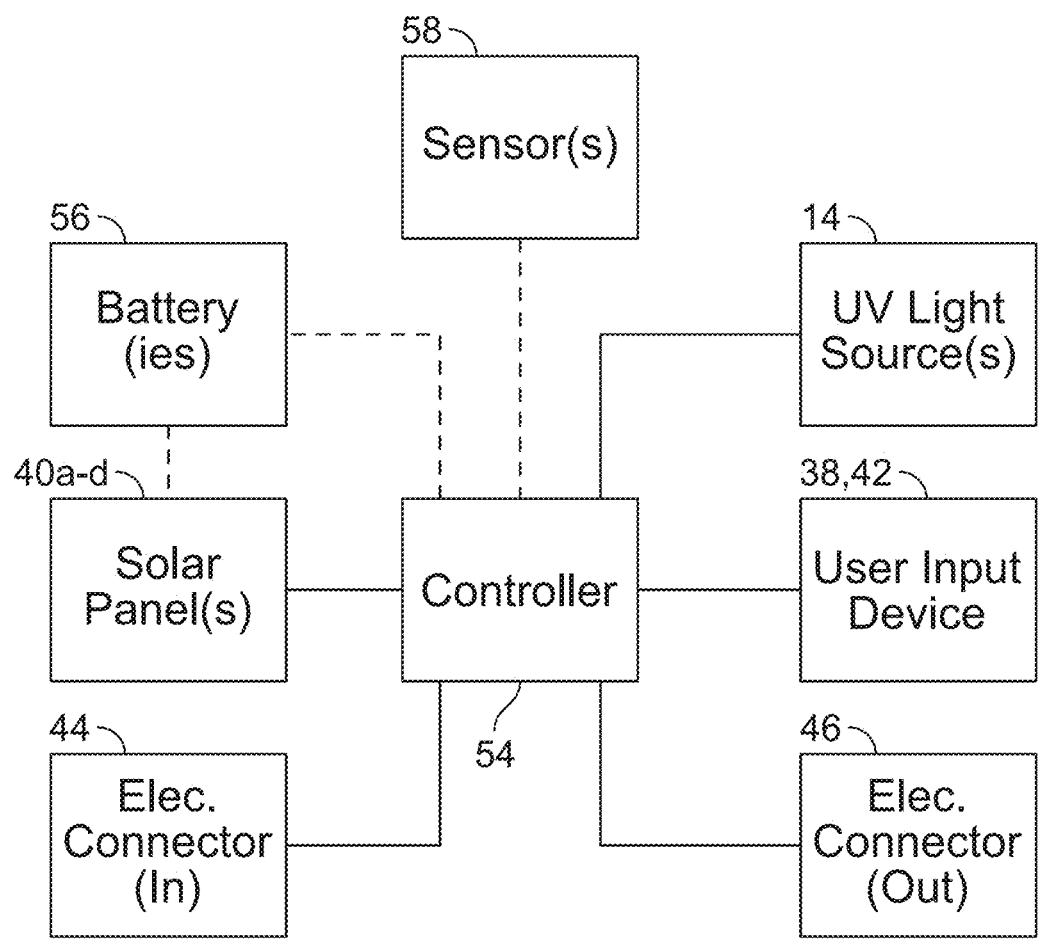
FIG. 5 is a schematic showing a control system of the sanitizer of FIG. 1.

Referring now to FIG. 5, a schematic of the control system for the sanitizer 10 is shown and described below. The sanitizer 10 may include a controller 54 that is electrically connected to the UV light sources 14, buttons 38 and 42 (or other user input devices), electrical connectors 44 and 46, solar panels 40*a-d*, one or more batteries 56, and one or more sensors 58. The controller 54, UV light sources 14, buttons 38 and 42 (or other user input devices), electrical connectors 44 and 46, solar panels 40*a-d*, one or more batteries 56, and one or more sensors 58 may be electrically connected to each other via flat flexible cables or flexible ribbon wiring positioned inside of the base 12 (e.g., between two sheets of material that form the front and rear surfaces 16 and 18 of the base 12). The controller 54 may further be positioned inside of the base 12. The controller 54 may be a control circuit that includes one or more processors (such as microprocessors, microcontrollers, etc.), one or more memories, and/or the like that are configured to control operation of the sanitizer 10. The controller 54 may be or include a central processing unit (CPU) that may be or include any computing device, memory, module, component, or the like that is configured to control operation of the sanitizer 10, including the functions described below.

When one of the buttons 38 and 42 is pressed and the UV light sources 14 are off, the controller 54 may connect the electrical connector 44, solar panels 40*a-d*, and/or batteries 56 to the UV light sources 14 to provide them with power and turn them on. After one of the buttons 38 or 42 is pressed, the controller 54 may be programmed to wait a predetermined amount of time before turning the UV light sources 14 on. For example, the controller 54 may be programmed to wait 30 seconds before turning the UV light sources 14 on so that a user has sufficient time to exit the vehicle and close the doors before the UV light sources 14 are turned on. The controller 54 may be programmed to turn the UV light sources 14 on for a predetermined period of time comprising a sanitation cycle after one of the buttons 38 or 42 is pressed. For example, the predetermined amount of time may be based on the amount of time estimated to effectively sanitize the interior of a vehicle when the sanitizer 10 is placed to cover the vehicle's windshield. The time may be estimated based on the number of UV light sources 14 and the amount of radiation emitted from the UV light sources 14. In some embodiments, the UV light sources 14 may be selected so that the predetermined amount of time is approximately 1 minute or less. Once the predetermined amount of time has expired, the controller 54 may turn the UV light sources 14 off. Alternatively, if a user presses one of the buttons 38 or 42 before the predetermined amount of time has expired, the controller 54 may turn the UV light sources 14 off when the button 38 or 42 is pressed. The buttons 38 and 42 may include an indicator light (not shown) to indicate when the UV light sources 14 are on. For example, the buttons 38 and 42 may flash a blue light when the UV light sources 14 are on. The buttons 38 and 42 may flash no light when the UV light sources 14 are off. The buttons 38 and 42 may flash a red light when the batteries 56 are low.

If a source of power is connected to electrical connector 44, the controller 54 may sense the connection and connect the electrical connector 44 to the batteries 56 for storage of the electrical power input through the electrical connector 44. If the UV light sources 14 are on while a source of power is connected to electrical connector 44, the controller 54 may connect the electrical connector 44 to the UV light sources 14. If an external device is connected to electrical connector 46, the controller 54 may sense the connection and deliver power from batteries 56 to the electrical connector 46 for powering the external device. If the solar panels 40*a-d* are generating electrical power, the controller 54 may connect the solar panels 40*a-d* to the batteries 56 for storing the power generated. Alternatively, the batteries 56 may be directly connected to or integrated with the solar panels 40*a-d* bypassing the controller 54. The solar panels 40*a-d* may have their own battery or batteries that are separate from the batteries 56. If the UV light sources 14 are on, the controller 54 may connect the solar panels 40*a-d* to the UV light sources 14 to deliver electrical power generated by the solar panels 40*a-d* to the UV light sources 14.

The sensor(s) 58 may be coupled to the base 12, e.g., the sensor(s) 58 may be coupled to the front surface 16 of the base 12. The sensor(s) 58 may be configured to sense when a person is near the base 12 and transmit a safety signal to the controller 54 when sensing that a person is near the base 12. If the UV light sources 14 are on when the safety signal is received by the controller 54, the controller 54 may turn off the UV light sources 14. The sensor(s) 58 may be any suitable type of sensors that are configured to detect when a person is near the base. For example, the sensor(s) 58 may include one or more of motion sensor(s) and/or temperature sensor(s). If motion is detected in front of the front surface 16 of the base 12 while the UV light sources 14 are on, the sensor(s) 58 and controller 54 may cause the UV light sources 14 to be turned off. Likewise, if a temperature indicative of a person or animal is sensed in front of the front surface 16 of the base 12 while the UV light sources 14 are on, the sensor(s) 58 and controller 54 may cause the UV light sources 14 to be turned off. Further, the sensor(s) 58 may be configured to detect acceleration. For example, if the sanitizer 10 is knocked over when in the position shown in FIGS. 3-4, or falls off of a vehicle's windshield, when in the position shown in FIGS. 1-2, the sensor(s) 58 may transmit the safety signal to the controller 54 to turn off the UV light sources 14.

In use, the sanitizer 10 may be placed in front of a vehicle's windshield in the interior of the vehicle to both block incoming sunlight through the windshield and sanitize surfaces within the vehicle and items placed within the vehicle. The sanitizer 10 may be placed on the dashboard of a vehicle and retained in place by the vehicle's rearview mirror. The vehicle's sun visors may further be flipped down to help retain the sanitizer 10 in place in front of the windshield. The electrical connector 44 may be connected to a wire that is connected on the opposite end to a power output port of the vehicle (e.g., a cigarette lighter socket or USB port). The user may then press one of the buttons 38 or 42 to turn on the UV light sources 14 as described above. As described above, the controller 54 may be programmed to turn the UV light sources 14 on to begin a sanitation cycle after a predetermined amount of time has elapsed (e.g., 30 seconds) to give the user time to exit the vehicle safely before the UV light sources 14 are turned on.

The UV light emitted by the UV light sources 14 sanitizes surfaces within the interior of the vehicle and items placed within the vehicle. For example, the UV light kills germs, bacteria, pathogens, and the like that may be present on surfaces within the vehicle and items placed within the vehicle. When the predetermined amount of time for the sanitation cycle is complete, the UV light sources 14 turn off and the interior surfaces of the vehicle and items placed within the vehicle are free of germs, bacteria, pathogens, and the like. Vehicle surfaces that may be sanitized by sanitizer 10 include, but are not limited to, seats, cup holders, glove box, center console, steering wheel, gear shift knob, and buttons.

To use the sanitizer 10 in the position shown in FIGS. 3 and 4, the sanitizer 10 is folded into a cylinder and straps 34a-c and 36a-c are connected to each other. The bottom row 30c is flipped outward to support the sanitizer 10 on a surface (e.g., seat or floor of a vehicle) and the top row 30a is flipped inward to support the lid 50. Items to be sanitized are placed within the interior cavity 48 (e.g., grocery bags 52). The lid 50 is placed on the top row 30a to cover the interior cavity 48 and items placed therein. The sanitizer 10 may then be operated as described above to sanitize the items placed within the interior cavity 48.

While the sanitizer 10 is shown in the Figures and described above as being configured for placement in front of a vehicle's windshield, it is within the scope of the invention disclosed herein for the sanitizer 10 to be sized and configured for placement over any window of a vehicle (e.g., a window in a vehicle door or a rear window of a vehicle). Further, while the sanitizer 10 is shown and described above as being in the general configuration of a foldable windshield sunshade, the sanitizer 10 may be configured so that it is in the form of a different type of sunshade. For example, the sanitizer 10 may be configured as an accordion or pleated sunshade. In such a configuration, the sanitizer 10 may have a housing with the accordion or pleated fabric being extendable from the housing to cover a window and retractable back to the housing for storage when not in use. The UV light sources 14 described above are positioned on the fabric, which acts as the base 12 described above, to emit UV light into the interior of the vehicle when the fabric is extended from the housing. The sanitizer 10 may further be configured as a retractable sunshade, e.g., a sunshade with a flexible sheet of material that winds around a cylinder when stored and extends away from the cylinder when deployed to cover a window. The UV light sources 14 described above are positioned on the flexible sheet of material, which acts as the base 12 described above, to emit UV light into the interior of the vehicle when the sheet of material is extended from the cylinder.

In another embodiment within the scope of the invention described herein, the sanitizer 10 may be formed like a blanket or sheet of material, which is flexible and foldable and has no appreciable rigid or semi-rigid sections. In such a configuration, the sanitizer 10 may appear similar to as shown in FIGS. 1 and 2 except that there is no cutout 28 for the rearview mirror. Further, there are no alternating rigid or semi-rigid sections 30 and flexible sections 32. Instead, substantially the entire base 12 of the sanitizer 10 is flexible like a typical blanket or sheet. Solar panels 40a-d may be omitted as desired. When in a blanket configuration with a base 12 that is substantially entirely flexible across its length and width, the sanitizer 10 may be used by draping it over surfaces or items that a user desires to sanitize. Otherwise, the sanitizer 10 may operate as described above.

Figure 6:
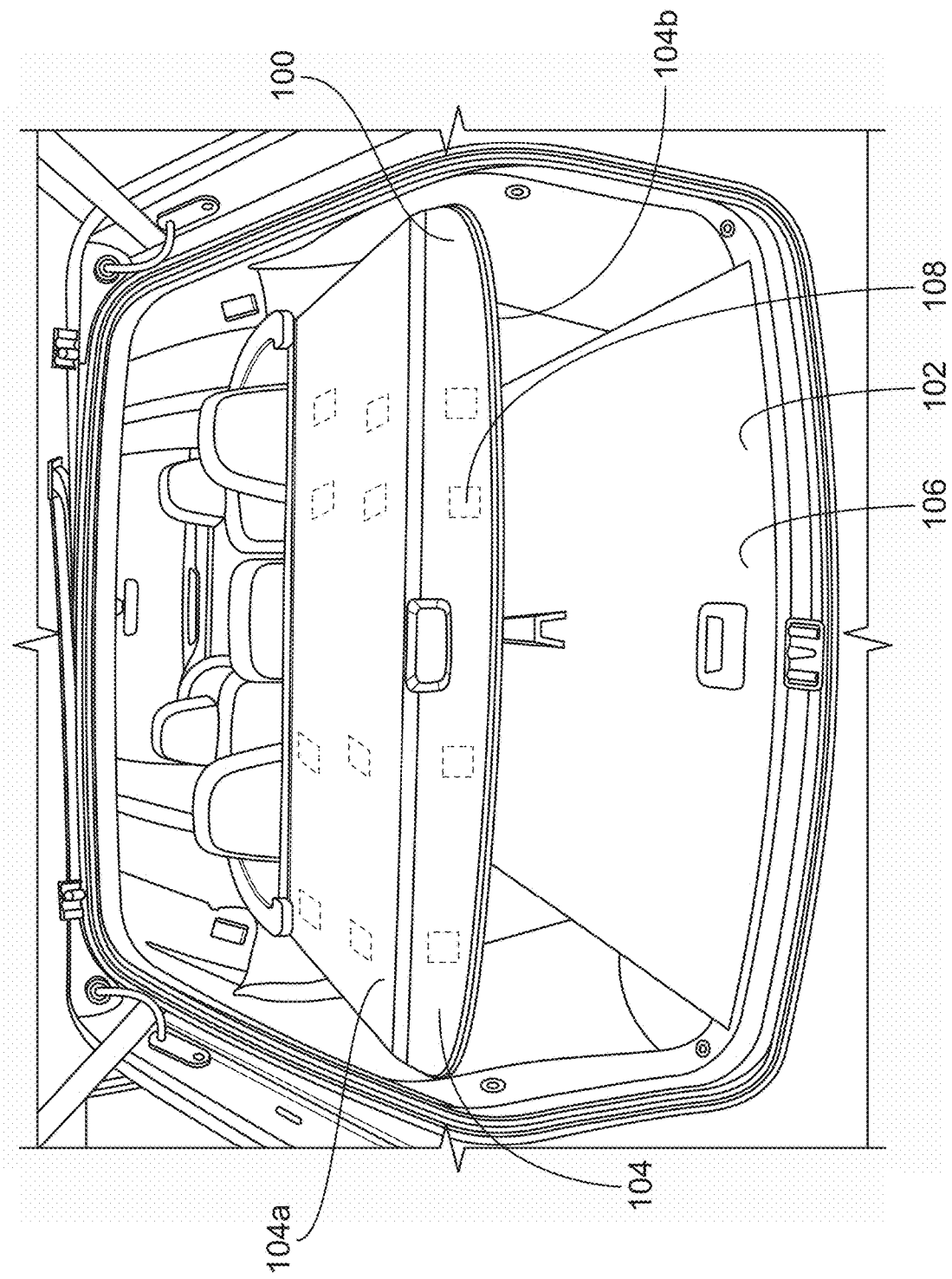
FIG. 6 is a perspective view of a sanitizer in accordance with an alternative embodiment of the invention described herein for use to sanitize the rear cargo compartment of a vehicle and items stored therein.

Referring now to FIG. 6, an alternative embodiment of sanitizer 100 in accordance with the invention described herein is operable to sanitize the rear cargo compartment 102 of a vehicle and any items stored therein. The sanitizer 100 is in the form of a cargo cover that covers a portion of the rear cargo compartment 102 of the vehicle. The vehicle shown is a typical SUV with a cargo area positioned behind rear seats of the vehicle and accessible by opening the tailgate of the vehicle. The sanitizer 100 has a base 104. The base 104 has a top side 104a and bottom side 104b. The base 104 is shown in FIG. 6 in a deployed position, in which a peripheral edge of the bottom side 104b rests on a ledge (not shown) within the vehicle to position the base 104 above the floor 106 of the vehicle within the rear cargo compartment 102. The base 104 is movable to an access position, in which the base 104 may be removed from the vehicle for storage so that the rear cargo compartment 102 is accessible. Alternatively, the base 104 may be folded or rolled up to the access position so that it no longer covers all or a substantial portion of the rear cargo compartment 102.

UV light sources, one of which is identified as 108 in FIG. 6, are attached to the bottom side 104b of the base 104 so that they face the floor 106 of the rear cargo compartment 102 beneath the sanitizer 100 when the base 104 is in the deployed position. The UV light sources 108 are shown in dashed lines in FIG. 6 to indicate that they are on the bottom side 104b of the base 104. The UV light sources 108 are joined to the base 104 so that when the base 104 is in the deployed position, UV light emitted from the UV light sources 108 is emitted into the rear cargo compartment 102 beneath the base 104. The UV light sources 108 may be substantially the same as the UV light sources 14 described above and operate in substantially the same manner as the UV light sources 14 described above.

The sanitizer 100 may include a control system that is substantially the same as the control system of sanitizer 10 shown in FIG. 5 and described above. The control system of sanitizer 100 may further operate in substantially the same manner as described above with respect to sanitizer 10. The sanitizer 100 may be used to sanitize the rear cargo compartment 102 of the vehicle shown in FIG. 6, and items placed within the rear cargo compartment 102, in substantially the same manner as described above with respect to sanitizer 10.

Figure 7:
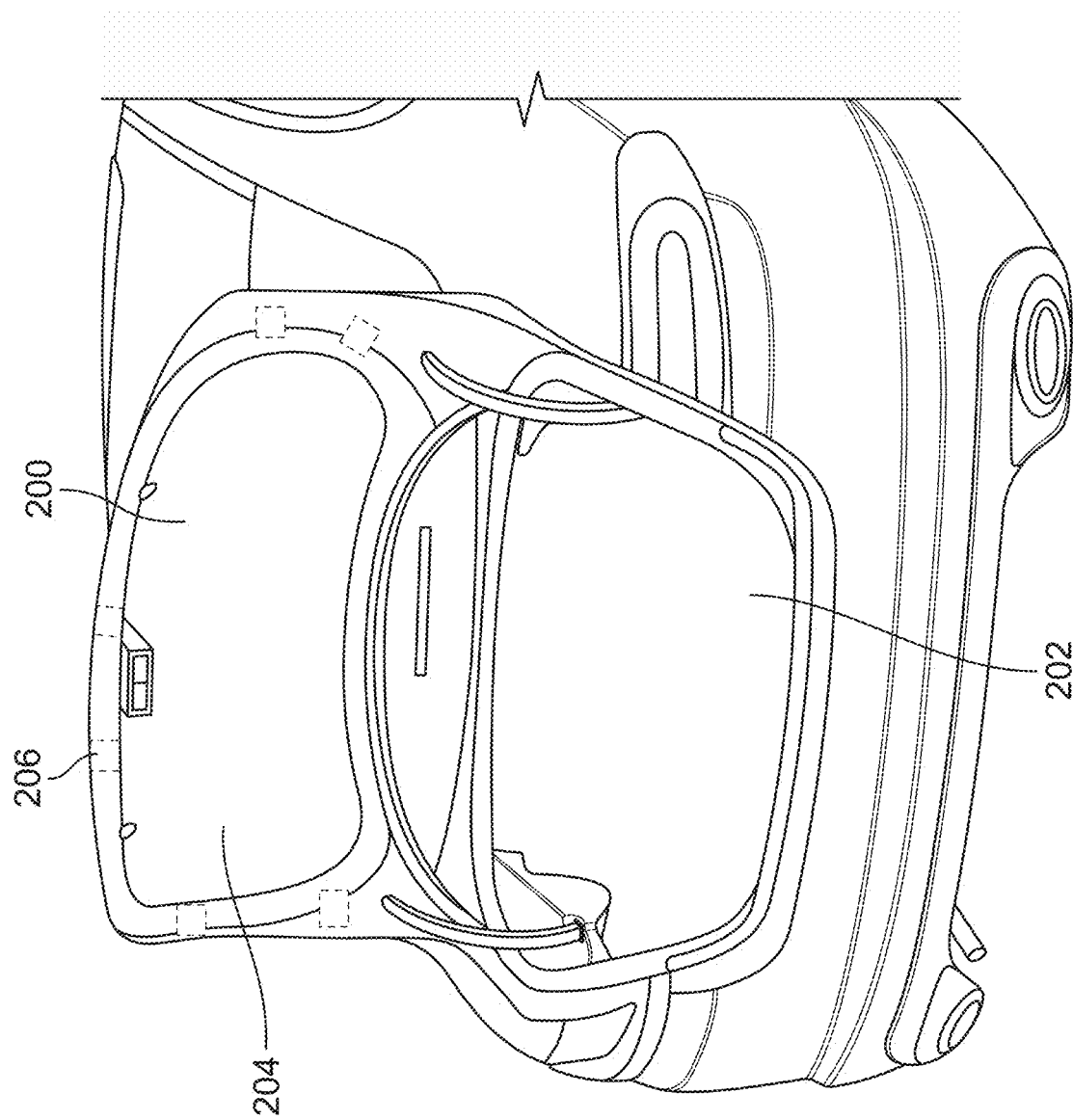
FIG. 7 is a perspective view of a sanitizer in accordance with another alternative embodiment of the invention described herein for use to sanitize the trunk of a vehicle and items stored therein.

Referring now to FIG. 7, an alternative embodiment of sanitizer 200 in accordance with the invention described herein is operable to sanitize the trunk 202 of a vehicle and any items stored therein. The sanitizer 200 is in the form of a trunk lid or liner attached to the underside of the trunk lid that is operable to cover the trunk 202 of the vehicle. The vehicle shown is a typical automotive sedan with a cargo area positioned behind rear seats of the vehicle and accessible by opening the trunk lid of the vehicle. The sanitizer 200 has a base 204, which forms an interior lining of the trunk lid or an integral portion of the trunk lid. The base 204 has a bottom side that faces the interior of the trunk 202 when the trunk lid is shut. The base 204 is shown in FIG. 7 in an access position, in which the trunk 202 of the vehicle is accessible. As known, the trunk lid along with the base 204 is rotatable downward to a deployed position, in which it covers the trunk 202 of the vehicle.

UV light sources, one of which is identified as 206 in FIG. 7, are attached to the bottom side of the base 204 so that they face the trunk 202 of the vehicle beneath the sanitizer 200 when the base 204 is in the deployed position covering the trunk 202. The UV light sources 206 are joined to the base 204 so that when the base 204 is in the deployed position, UV light emitted from the UV light sources 206 is emitted into the trunk 202 beneath the base 204. The UV light sources 206 may be substantially the same as the UV light sources 14 described above and operate in substantially the same manner as the UV light sources 14 described above.

The sanitizer 200 may include a control system that is substantially the same as the control system of sanitizer 10 shown in FIG. 5 and described above. The control system of sanitizer 200 may further operate in substantially the same manner as described above with respect to sanitizer 10. The sanitizer 200 may be used to sanitize the trunk 202 of the vehicle shown in FIG. 7, and items placed within the trunk 202, in substantially the same manner as described above with respect to sanitizer 10.

Figure 8:
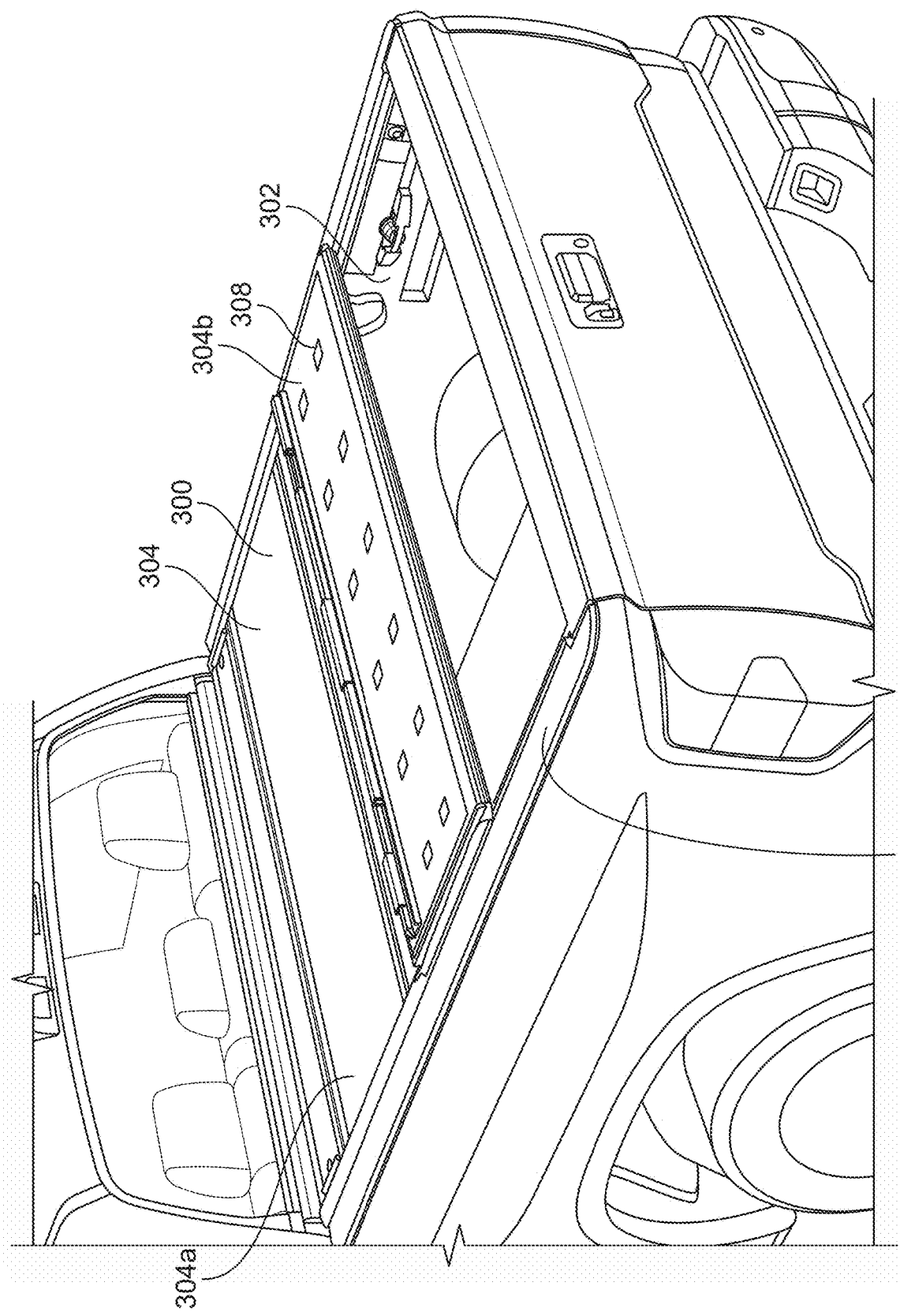
FIG. 8 is a perspective view of a sanitizer in accordance with another alternative embodiment of the invention described herein for use to sanitize the truck bed of a vehicle and items stored therein.

FIG. 8 shows an alternative embodiment of sanitizer 300 in accordance with the invention described herein. Sanitizer 300 is operable to sanitize a truck bed compartment 302 of a vehicle and any items stored therein. The sanitizer 300 is in the form of a truck bed cover that is operable to cover the truck bed compartment 302 of the vehicle. The vehicle shown is a typical pickup truck with a truck bed positioned behind a cab of the vehicle. The sanitizer 300 has a base 304. The base 304 has a top side 304a and bottom side 304b. The base 304 is shown in FIG. 8 in a partially deployed position, in which a peripheral edge of a portion of the bottom side 304b rests on an upper edge 306 of side walls forming the truck bed compartment 302. The base 304 is shown as a folding truck bed cover, which has segments that can fold up to uncover portions of the truck bed compartment 302. The rearmost segment is shown in a folded or access position in FIG. 8, in which it rests on top of the segment positioned forward of it and exposing its bottom side 304b. Additional segments of the base 304 may further be folded forward to expose more of the truck bed compartment 302, and the base 304 may also be removable from the vehicle entirely or in segments to expose the entire or portions of the truck bed compartment 302. The rearmost segment of the base 304 may further be folded back down from the position shown in FIG. 8 so that the base 304 is in a fully deployed position, in which it covers substantially the entire truck bed compartment 302 and any items positioned therein. Although sanitizer 300 is shown as a folding truck bed cover, it is within the scope of the invention described herein for the sanitizer 300 to be a roll-up truck bed cover that rolls from a deployed position, in which it covers substantially the entire truck bed compartment 302, to an access position, in which it is positioned adjacent the rear of the cab of the vehicle on top of the front of the truck bed compartment 302.

UV light sources, one of which is identified as 308 in FIG. 8, are attached to the bottom side 304b of the base 304 so that they face the truck bed compartment 302 beneath the sanitizer 300 when the base 304 is in the deployed position. The UV light sources 308 are joined to the base 304 so that when the base 304 is in the deployed position, UV light emitted from the UV light sources 308 is emitted into the truck bed compartment 302 beneath the base 304. The UV light sources 308 may be substantially the same as the UV light sources 14 described above and operate in substantially the same manner as the UV light sources 14 described above.

The sanitizer 300 may include a control system that is substantially the same as the control system of sanitizer 10 shown in FIG. 5 and described above. The control system of sanitizer 300 may further operate in substantially the same manner as described above with respect to sanitizer 10. The sanitizer 300 may be used to sanitize the truck bed compartment 302 of the vehicle shown in FIG. 8, and items placed within the truck bed compartment 302, in substantially the same manner as described above with respect to sanitizer 10.

Figure 9:
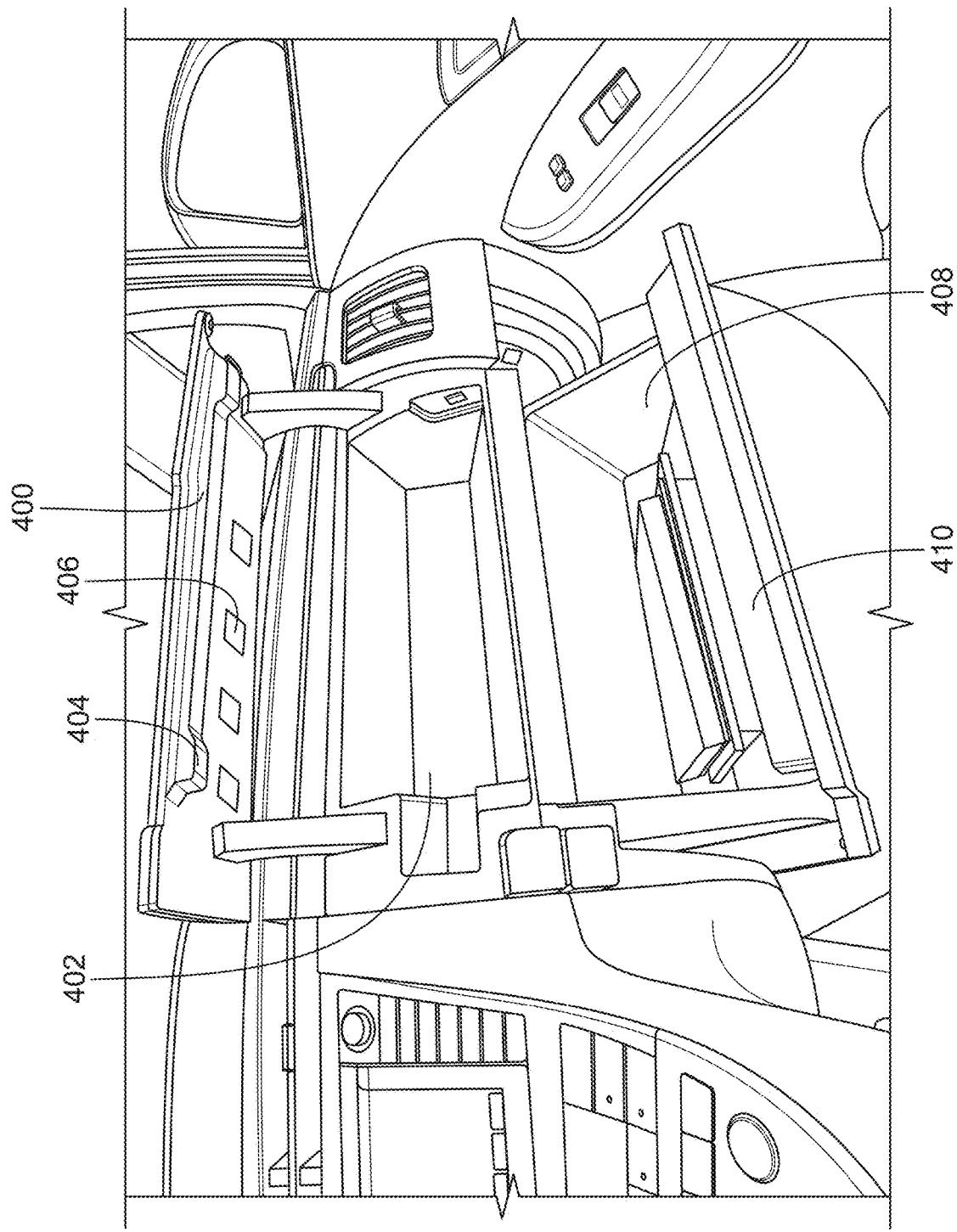
FIG. 9 is a perspective view of a sanitizer in accordance with another alternative embodiment of the invention described herein for use to sanitize the glove box of a vehicle and items stored therein.

Referring now to FIG. 9, an alternative embodiment of sanitizer 400 in accordance with the invention described herein is operable to sanitize the glove box 402 of a vehicle and any items stored therein. The sanitizer 400 is in the form of a glove box door that is operable to cover the glove box 402 of the vehicle. The sanitizer 400 has a base 404, which may be an integral portion of the glove box door. The base 404 has a bottom side that faces the interior of the glove box 402 when the glove box door is shut. The base 404 is shown in FIG. 9 in an access position, in which the glove box 402 of the vehicle is accessible. As known, the base 404 is moveable to a deployed position, in which it covers the glove box 402 of the vehicle.

UV light sources, one of which is identified as 406 in FIG. 9, are attached to the bottom side of the base 404 so that they face the glove box 402 of the vehicle behind the sanitizer 400 when the base 404 is in the deployed position covering the glove box 402. The UV light sources 406 are joined to the base 404 so that when the base 404 is in the deployed position, UV light emitted from the UV light sources 406 is emitted into the glove box 402 behind the base 404. The UV light sources 406 may be substantially the same as the UV light sources 14 described above and operate in substantially the same manner as the UV light sources 14 described above.

The sanitizer 400 may include a control system that is substantially the same as the control system of sanitizer 10 shown in FIG. 5 and described above. The control system of sanitizer 400 may further operate in substantially the same manner as described above with respect to sanitizer 10. The sanitizer 400 may be used to sanitize the glove box 402 of the vehicle shown in FIG. 9, and items placed within the glove box 402, in substantially the same manner as described above with respect to sanitizer 10.

The vehicle shown in FIG. 9 further includes a second glove box 408, which may have a sanitizer 410 integrated into the glove box door that works in substantially the same manner as described above with respect to sanitizer 400.

Figure 10:
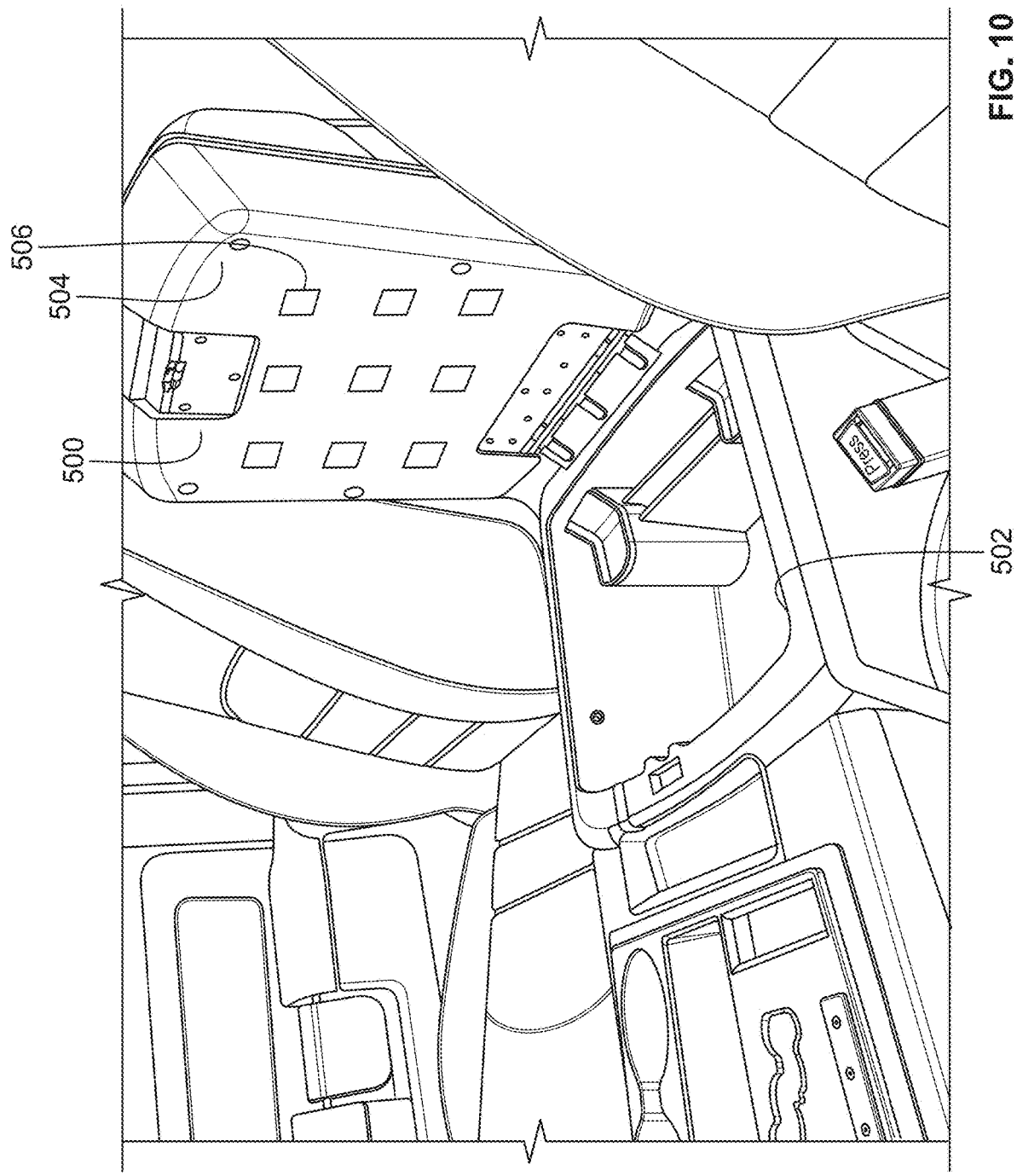
FIG. 10 is a perspective view of a sanitizer in accordance with another alternative embodiment of the invention described herein for use to sanitize the center console of a vehicle and items stored therein.

Referring now to FIG. 10, an alternative embodiment of sanitizer 500 in accordance with the invention described herein is operable to sanitize the center console compartment 502 of a vehicle and any items stored therein. The sanitizer 500 is in the form of a center console cover that is operable to cover the center console compartment 502 of the vehicle. The sanitizer 500 has a base 504, which may be formed integral with a lower surface of the center console cover. The base 504 has a bottom side that faces the center console compartment 502 when the base 504 is shut. The base 504 is shown in FIG. 10 in an access position, in which the center console compartment 502 of the vehicle is accessible. As known, the base 504 is rotatable downward to a deployed position, in which it covers the center console compartment 502 of the vehicle.

UV light sources, one of which is identified as 506 in FIG. 10, are attached to the bottom side of the base 504 so that they face the center console compartment 502 of the vehicle beneath the sanitizer 500 when the base 504 is in the deployed position covering the center console compartment 502. The UV light sources 506 are joined to the base 504 so that when the base 504 is in the deployed position, UV light emitted from the UV light sources 506 is emitted into the center console compartment 502 beneath the base 504. The UV light sources 506 may be substantially the same as the UV light sources 14 described above and operate in substantially the same manner as the UV light sources 14 described above.

The sanitizer 500 may include a control system that is substantially the same as the control system of sanitizer 10 shown in FIG. 5 and described above. The control system of sanitizer 500 may further operate in substantially the same manner as described above with respect to sanitizer 10. The sanitizer 500 may be used to sanitize the center console compartment 502 of the vehicle shown in FIG. 10, and items placed within the center console compartment 502, in substantially the same manner as described above with respect to sanitizer 10.

Although FIGS. 5-10 show specific storage compartments of a vehicle that may be sanitized using the sanitizers 100, 200, 300, 400, and 500 described herein, it is within the scope of the invention to use any of the sanitizers described herein to sanitize any storage compartment of a vehicle.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A sanitizer comprising:

a base that is at least one of flexible or foldable, wherein the base is configured to be removably placed over a window of a vehicle, wherein the base is foldable, wherein the base includes a top edge, a bottom edge, a first side edge, and a second side edge, wherein the base is foldable from a first position in which it is generally planar into a second position in which it is generally cylindrical and the first side edge is positioned adjacent the second side edge, wherein the base includes a plurality of rigid or semi-rigid sections and a plurality of flexible sections, wherein the plurality of flexible sections includes a plurality of flexible sections each extending from adjacent the bottom edge to adjacent the top edge, and wherein the plurality of rigid or semi-rigid sections includes a plurality of sections each positioned between one of the flexible sections and one of the first side edge or the second side edge or between two of the flexible sections, wherein the plurality of flexible sections includes a bottom flexible section that is spaced apart from the bottom edge and that extends from adjacent the first side edge to adjacent the second side edge, wherein the plurality of rigid or semi-rigid sections includes at least one bottom section positioned between the bottom edge and the bottom flexible section, wherein the bottom flexible section is configured so that the at least one bottom section may be folded to extend laterally outward from an adjacent portion of the base; and an ultraviolet (UV) light source configured to emit UV light, the UV light source coupled to the base.

2. The sanitizer of claim 1, wherein the UV light source is configured to emit UV germicidal irradiation and comprises one or more of a low pressure mercury discharge lamp, one or more fiber optic couplings, or one or more light emitting diodes.

3. The sanitizer of claim 1, further comprising a first attachment structure coupled to the base adjacent the first side edge and a second attachment structure coupled to the base adjacent the second side edge, wherein the first attachment structure is configured to releasably attach to the second attachment structure.

4. The sanitizer of claim 1, wherein the base is a flexible sheet of material.

5. The sanitizer of claim 1, further comprising a battery coupled to the base, wherein the battery is electrically coupled to the UV light source.

6. The sanitizer of claim 5, further comprising at least one solar panel coupled to the base, wherein the solar panel is electrically coupled to the battery.

7. The sanitizer of claim 1, further comprising a controller electrically coupled to the UV light source, and a sensor coupled to the base and electrically coupled to the controller, wherein the sensor is configured to detect when a person is near the base and transmit a safety signal to the controller, and wherein the controller is configured to turn off the UV light source when it receives the safety signal.

* * * * *